(12) United States Patent
Kaneko et al.

(10) Patent No.: US 6,635,674 B1
(45) Date of Patent: Oct. 21, 2003

(54) PHARMACEUTICAL PREPARATIONS FOR EXTERNAL USE CONTAINING NON-STEROIDAL ANTI-INFLAMMATORY AND ANALGESIC AGENTS

(75) Inventors: Teruhisa Kaneko, Tokyo (JP); Yuka Shinohara, Tokyo (JP); Yoko Kawamura, Tokyo (JP); Masaaki Nagase, Hachioji (JP)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/831,081

(22) PCT Filed: Oct. 28, 1999

(86) PCT No.: PCT/US99/25555

§ 371 (c)(1),
(2), (4) Date: May 2, 2001

(87) PCT Pub. No.: WO00/27372

PCT Pub. Date: May 18, 2000

(30) Foreign Application Priority Data

Nov. 6, 1998 (JP) ............................................ 10-315739

(51) Int. Cl.$^7$ .................... A61K 31/192; A61K 31/195; A61K 31/045
(52) U.S. Cl. .......................... 514/562; 514/729; 424/40
(58) Field of Search ................................. 514/562, 729

(56) References Cited

U.S. PATENT DOCUMENTS

| 5,434,292 A | 7/1995 | Saita et al. |
| 5,827,886 A | 10/1998 | Hersh |

FOREIGN PATENT DOCUMENTS

| EP | 0491076 A1 | 6/1992 |

OTHER PUBLICATIONS

Remington's Pharmaceutical Sciences, Mack Publishing Co. Fifteenth edition, 1975, pp. 721–722.*

* cited by examiner

Primary Examiner—Frederick Krass
Assistant Examiner—Donna Jagoe
(74) Attorney, Agent, or Firm—Jonathon N. Provoost

(57) ABSTRACT

The present invention relates to an anti-inflammatory and analgesic pharmaceutical preparation for external use having excellent percutaneous absorption and applicability. The pharmaceutical preparations for external use of this invention comprise NSAIDs and, as a percutaneous absorption promoting agent, oleic acid, oleyl alcohol or a mixture thereof, in a pharmaceutically acceptable aqueous alcoholic solvent comprised of a monohydric saturated aliphatic alcohol of 1–4 carbon atoms, a polyhydric alcohol selected from the group consisting of saturated aliphatic glycols of 2–4 carbon atoms and glycerol, and water.

13 Claims, 1 Drawing Sheet

[Fig. 1]
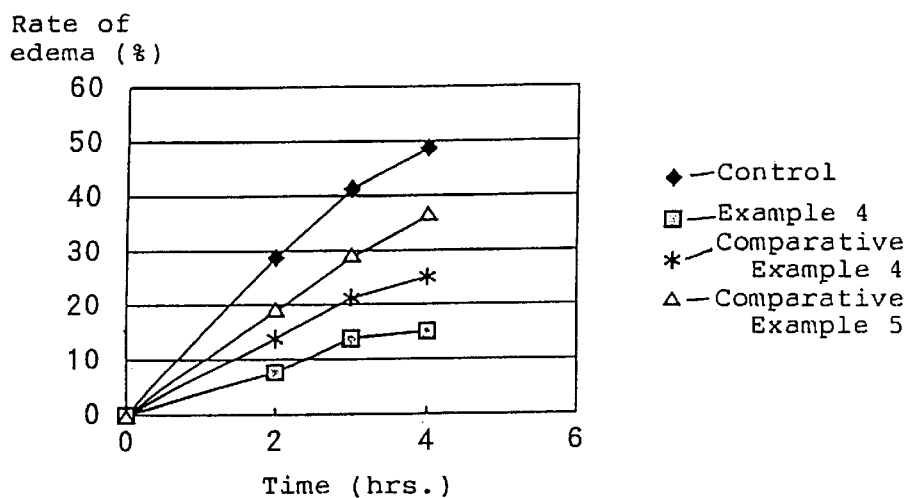
[Fig. 2]
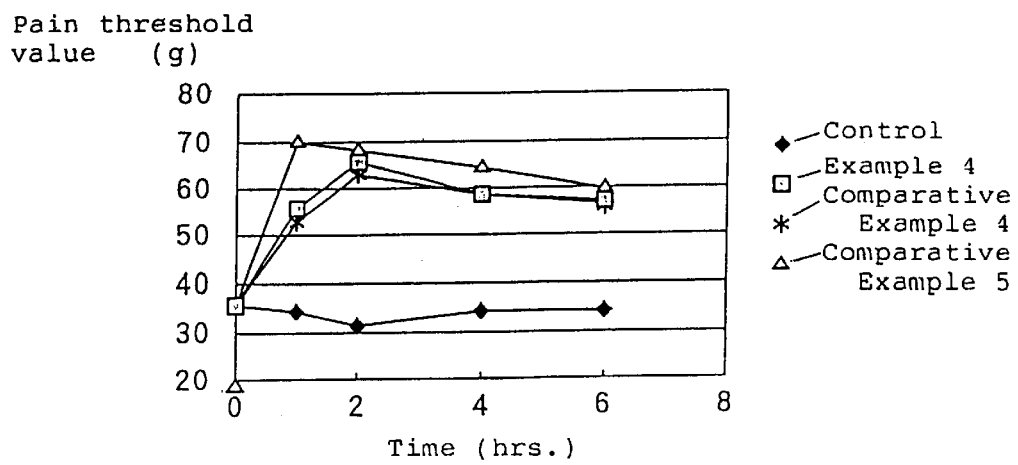

PHARMACEUTICAL PREPARATIONS FOR EXTERNAL USE CONTAINING NON-STEROIDAL ANTI-INFLAMMATORY AND ANALGESIC AGENTS

This application claims priority to PCT Application International No. PCT/US99/25555 filed Oct. 28, 1999 claiming priority to Japanese Application Ser. No. 10/315,739, both of which are incorporated herein by reference.

FIELD OF THE INVENTION

This invention relates to an anti-inflammatory and analgesic pharmaceutical reparation for external use having excellent percutaneous absorption and applicability.

BACKGROUND OF THE INVENTION AND PRIOR ART

Non-steroidal anti-inflammatory and analgesic agents have an excellent anti-inflammatory and analgesic activity and have been widely used clinically in such dosage forms as ointments, gels, creams, lotions, adhesive plasters, capsules, suppositories and injections.

It has been hitherto common that non-steroidal anti-inflammatory and analgesic agents (hereinafter referred to as NSAIDs) have been orally administered in the dosage form of capsules, tablets, etc. Although oral dosage forms can be very effective when absorbed from the gastrointestinal tract, they can produce significant side effects. Therefore, oral dosage forms must be used with careful monitoring. Accordingly, to reduce side effects, such as gastrointestinal disorders, topical dosage forms have been developed, for example, gels (Japanese Patent Kokai Application No. 161323/1981), creams (Japanese Patent Kokai Application Nos. 103811/1983 and 298526/1987), ointments (Japanese Patent Kokai Application No. 39616/1983), adhesive plasters (Japanese Patent Kokai Application No. 250317/1989) and others. However, these prior art inventions have not resolved the problems of poor diffusion and transfer of the NSAIDs in the base phase of the adhesive plasters and inadequate drug release and percutaneous absorption from ointments (gel bases).

PROBLEMS TO BE SOLVED BY THE INVENTION

Accordingly, it is an object of this invention to provide a cutaneous pharmaceutical preparation for external use wherein the percutaneous absorption of NSAIDs is improved.

MEANS TO SOLVE THE PROBLEMS

As a result of intensive studies carried out by the present inventors, it has been discovered that the percutaneous absorption of an NSAID is significantly improved by adding to a specific water-soluble base a percutaneous absorption promoting agent selected from the group consisting of oleic acid, oleyl alcohol and mixtures thereof.

More specifically, the present invention relates to a pharmaceutical preparation for external use which comprises an NSAID and as a percutaneous absorption promoting agent, oleic acid, oleyl alcohol or a mixture thereof, in a pharmaceutically acceptable aqueous alcoholic solvent.

MODE FOR CARRYING OUT THE INVENTION

As the aqueous alcoholic solvent employed in this invention, there may be preferably mentioned a homogeneous mixed solvent comprising a monohydric saturated aliphatic alcohol of 1–4 carbon atoms; a polyhydric alcohol selected from the group consisting of saturated aliphatic glycols of 2–4 carbon atoms, glycerol and mixtures thereof; and water.

As the monohydric saturated aliphatic alcohol, there may be mentioned: methanol, ethanol, n-propanol, isopropanol and the like. Ethanol and isopropanol are particularly preferred.

As the saturated aliphatic glycol, there may be mentioned: ethylene glycol, propylene glycol, 1,3-butylene glycol, isopropylene glycol (3-methyl-1,3-butanediol) and the like.

As the polyhydric alcohol, there may be mentioned: said saturated aliphatic glycol of 2–4 carbon atoms and/or glycerol. Glycerol is particularly preferred.

A preferable blended proportion of such aqueous alcoholic solvent is 15–70% by weight, more preferably 30–65% by weight, for the monohydric saturated alcohol, 0.1–30% by weight, more preferably 0.5–15% by weight, for the polyhydric alcohol and 10–60% by weight preferably 20–50% by weight, for water. When the proportion of the monohydric saturated aliphatic alcohol is too low, solubility of the NSAIDs is lowered, whereby turbidity appears and stability is decreased. The polyhydric alcohol, more preferably glycerol, may be preferably used at 5–30% by weight to the said monohydric saturated alcohol while satisfying said blended proportion.

It is essential in this invention to combine the specified aqueous alcoholic solvent with oleic acid and/or oleyl alcohol. These percutaneous absorption promoting agents may be used alone or in combination.

Oleic acid is preferred and cis-oleic acid is most preferred. A blended proportion of such percutaneous absorption promoting agents is 0.1–15% by weight. preferably, 0.5–10% by weight, based on the total weight of the preparation for external use. If it is too low, a promoting effect on percutaneous absorption will not be obtained.

Increasing the concentration of the percutaneous absorption promoting agent above 15% does not afford a significant improvement in percutaneous absorption.

The NSAID may be preferably employed at a concentration of 0.1–10% by weight, more preferably at a concentration of 0.5–5% by weight, based upon the total weight of the preparation for external use.

It is preferable for the anti-inflammatory and analgesic preparation for external use to further incorporate therein menthol, especially 1-menthol. Menthol may be employed in a concentration of 0.5–5% by weight, based upon the total weight of the preparation for external use.

The anti-inflammatory and analgesic pharmaceutical preparation of this invention may be preferably applied in the dosage form of liquids or gels as such dosage forms permit more effective use of the present invention. These dosage forms may use conventional bases and blending components compliant with the desired dosage form. As the water-soluble polymers which may be commonly used as a gelling agent there may be mentioned, for example, carboxyvinyl polmer, sodium carboxymethylcellulose, polyvinyl alcohol, methylcellulose, hydroxyethylcellulose, hydroxypropylcellulose, polyvinylpyrrolidone, hydroxypropylmethylcellulose, etc. The gelling agent may be employed in a concentration of 0.1–5% by weight, based upon the total weight of the preparation for external use.

If required, humectants, antiseptics, antioxidants, coloring agents, perfumes, thickening agents, etc., may optionally be added to the anti-inflammatory and analgesic pharmaceutical preparation of this invention.

EFFECT OF THE INVENTION

In accordance with this invention, there is provided a cutaneous, NSAID containing, topical pharmaceutical preparation that has excellent percutanous absorption. Significantly, the dermatologic, topical, NSAID containing pharmaceutical preparation of the present invention possesses excellent percutaneous absorptive properties and when used in therapy can reduce NSAID side effects, such as, gastrointestinal, hepatic and renal disorders caused by continued oral administration and avoid the pain accompanying NSAID injection. The use of the dermatologic topical preparations of the present invention affords potent therapeutic effects in chronic articular rheumatish, peritendinitis, muscle pain, swelling and pain after wounds, etc.

Percutaneous absorption effect, pharmacological effect and stimulation to the skin by the anti-inflammatory and analgesic pharmaceutical preparation for external use according to this invention will be explained in greater detail by way of the following examples.

EXAMPLES

The compositions of the following Examples 1–4 and Comparative Examples 1 and 2 were prepared by a conventional method. Commercially available ketophenol-containing dermatologic drugs for external use were used in Comparative Examples 3–5.

Lotion

Example 1

| | |
|---|---|
| Ethanol | 56% by weight |
| Ketoprofen | 3% by weight |
| 1-Menthol | 3% by weight |
| Oleic Acid | 0.8% by weight |
| Oleyl Alcohol | 4.2% by weight |
| Glycerol | 6% by weight |
| Water | 27% by weight |

Example 2

| | |
|---|---|
| Isopropanol | 56% by weight |
| Ketoprofen | 3% by weight |
| 1-Menthol | 3% by weight |
| Oleic Acid | 0.8% by weight |
| Oleyl Alcohol | 4.2% by weight |
| Glycerol | 6% by weight |
| Water | 27% by weight |

Example 3

| | |
|---|---|
| Ethanol | 50% by weight |
| Ketoprofen | 3% by weight |
| 1-Menthol | 3% by weight |
| Oleic Acid | 4% by weight |
| Glycerol | 6% by weight |
| Water | 34% by weight |

Gel

Example 4

| | |
|---|---|
| Ethanol | 56% by weight |
| Ketoprofen | 3% by weight |
| 1-Menthol | 3% by weight |
| Oleic Acid | 0.8% by weight |
| Oleyl Alcohol | 0.2% by weight |
| Glycerol | 5.7% by weight |
| Hydroxypropylcellulose | 0.5% by weight |
| Diisopropanolamine | 0.4% by weight |
| Water | 29.8% by weight |

Lotion

Example 5

| | |
|---|---|
| Ethanol | 56% by weight |
| Indomethacin | 1% by weight |
| 1-Menthol | 3% by weight |
| Oleic Acid | 0.8% by weight |
| Oleyl Alcohol | 4.2% by weight |
| Glycerol | 6% by weight |
| Water | 27% by weight |

Example 6

| | |
|---|---|
| Isopropanol | 56% by weight |
| Bufexamac | 1% by weight |
| 1-Menthol | 3% by weight |
| Oleic Acid | 0.8% by weight |
| Oleyl Alcohol | 4.2% by weight |
| Glycerol | 6% by weight |
| Water | 27% by weight |

Gel

Example 7

| | |
|---|---|
| Ethanol | 56.6% by weight |
| Ibuprofen | 2% by weight |
| 1-Menthol | 3% by weight |
| Oleic Acid | 0.8% by weight |
| Oleyl Alcohol | 0.2% by weight |
| Glycerol | 5.7% by weight |
| Hydroxypropylcellulose | 0.5% by weight |
| Diisopropanolamine | 0.4% by weight |
| Water | 29.8% by weight |

Lotion

Comparative Example 1

| | |
|---|---|
| Ethanol | 56% by weight |
| Ketoprofen | 3% by weight |
| 1-Menthol | 3% by weight |
| Glycerol | 6% by weight |
| Water | 32% by weight |

Comparative Example 2

| | |
|---|---|
| Ethanol | 71% by weight |
| Ketoprofen | 3% by weight |
| 1-Menthol | 3% by weight |
| Oleic Acid | 1% by weight |
| Oleyl Alcohol | 4% by weight |
| Glycerol | 18% by weight |

Comparative Example 3

Epatec A Lotion (Zeria-Nissan Chemical)

Comparative Example 4

Epatec A Gel (Zeria-Nissan Chemical)

Indomethacin-containing gel

Comparative Example 5

Vantelin Kowa Gel (Kowa)

Lotion

Comparative Example 6

| | |
|---|---|
| Ethanol | 56% by weight |
| Indomethacin | 1% by weight |
| 1-Menthol | 3% by weight |
| Oleic Acid | 0.8% by weight |
| Oleyl Alcohol | 4.2% by weight |

-continued

| | |
|---|---|
| Glycerol | 6% by weight |
| Water | 32% by weight |

Gel

Comparative Example 7

| | |
|---|---|
| Isopropanol | 56% by weight |
| Bufexamac | 1% by weight |
| 1-Menthol | 3% by weight |
| Glycerol | 6% by weight |
| Water | 34% by weight |

Lotion

Comparative Example 8

| | |
|---|---|
| Ethanol | 71% by weight |
| Bufexamac | 1% by weight |
| 1-Menthol | 3% by weight |
| Oleic Acid | 1% by weight |
| Oleyl Alcohol | 4% by weight |
| Glycerol | 18% by weight |

Test Examples for Evaluation

The NSAIDs containing pharmaceutical preparations of the above Examples and Comparative Examples were tested and their respective percutaneous absorption effect, pharmacological effect and stimulation to the skin were determined.

Test Example 1

Test on Skin Permeability in vitro

Hartley strain male guinea pigs 4 weeks of age were anesthetized with Nembutal by intraperitoneal injection and the hair on the back of the animal was clipped with a hair clipper. Then the skin was collected. Subcutaneous tissues were removed as much as possible from the collected skin without damaging the epidermis and the skin was cut into skin sheets of about 2 cm square. The sheets were placed in a Franz type diffusion cell having an effective diffusion area of 0.785 $cm^2$. The diffusion cell was kept at 37° C. by circulating water at a constant temperature and the side of receptor of the cell was filled with 5 ml of an aqueous solution containing 5% bovine serum albumin for receiving ketoprofen which is sparingly soluble in water. The skin was applied to the diffusion cell and allowed to stand for 2 hours until the system reached a stationary state then 1 ml of a test solution was placed on the donor side of the cell. In order to prevent evaporation of the solution from the donor side, it was tightly sealed with parafilm. Thereafter, 100 μl each of the aqueous solutions at the receptor side was sampled with lapse of time. Acetonitrile (500 μl) was added to the collected sample to precipitate and remove the bovine serum albumin and the liberated ketoprofen was determined by a conventional method using HPLC. The measurement parameters for the HPLC were as defined below:

Column (for ketoprofen); STR ODS-II(I.D.4.6 mm×L. 15 cm): Mobile phase; acetonitirile: 100 mM phosphate buffer=4:6: Flow rate; 1 ml/min.: Column temperature; 25° C.: Detection; 254 nm.

Column (for indomethacin); STR ODS-II(I.D.4.6 mm×L. 15 cm): Mobile phase; acetonitrile: 10 mM phosphate buffer=4:6: Flow rate; 10 ml/min.: Column temperature; 25° C.: Detection; 254 nm.

Column (for bufexamac); STR ODS-II(I.D.4.6 mm×L. 15 cm): Mobile phase; 2.5 g of sodium 1-octanesulfonate and 0.6 g of sodium ethylenetetraacetate were dissolved in 800 ml of water and to the solution were added 500 ml of methanol, 500 ml of acetonitrile and 8 ml of glacial acetic acid: Flow rate; 1.0 ml/min.: Column temperature; 25° C.: Detection; 254 nm.

Accumulated amounts of the NSAIDs which permeated through the skin to the receptor side after 12 hours from initiation of the test are shown in Table 1.

TABLE 1

Accumulated rate permeated through the skin

| | Permeated amount through the skin ($\mu g/cm^2$) |
|---|---|
| Ketoprofen 3% | |
| Example 1 | 812 |
| Example 2 | 910 |
| Example 3 | 775 |
| Comparative Example 1 | 35 |
| Comparative Example 2 | 158 |
| Comparative Example 3 | 258 |
| Indomethacin 1% | |
| Example 5 | 320 |
| Comparative Example 6 | 19 |
| Comparative Example 5 | 91 |
| Bufexamac 1% | |
| Example 6 | 279 |
| Comparative Example 3 | 21 |

Comparative Example 8

In the case of ketoprofen, the lotions of Examples 1–3 showed better percutaneous absorption than the lotion of Comparative Example 1 (which contained no oleic acid and no oleyl alcohol), the lotion of Comparative Example 2 (which contained no water) and the competitive lotion of Comparative Example 3. Similar results were obtained with both indomethacin and bufexamac. It is apparent from the above results that the anti-inflammatory and analgesic preparation for external use of the present invention significantly promotes the percutaneous absorption of NSAIDs.

Test Example 2

Test on Skin Pharmacological Effect Test on Inhibition of Edema Induced by Carrageenin Anti-inflammatory action of the anti-inflammatory and analgesic preparation for external use according to this invention (Example 4) and that of competitive products of another company (Comparative Examples 4 and 5) were evaluated as to their ability to inhibit carrageenin-induced edema. The volume of the right hind paws of rats of Wistar strain (male; eight weeks of age) was measured using a paw volume measuring device (MK-550; manufactured by Muromachi Kikai K.K.). The rats were then divided into five groups (each group consisting of eight rats) so that the mean value of paw volumes in each group was approximately equal. Each preparation (50 mg) was applied to the area around the site of the right hind paw to which the carrageenin was to be administered and, after 2 hours, the same amount was applied again to the same area. After 0.5 hours from the second application, the applied drug was removed using a gauge which was wetted with warm pure water and 0.08 ml of 1% carrageenin was immediately administered subcutaneously. After 2, 3 and 4 hours from the administration of the carrageenin, paw volumes were measured and the swelling rate was calculated from the difference between the paw volumes before and after application of the preparation. Incidentally, after application of the preparation, the administered site was covered with a wrapping film (Salan Wrap; manufactured by Asahi Chemical Industries Co., Ltd.) and an expandable adhesive tape (Silky Tex; manufactured by ALCARE) was applied thereon to fix it in place, so that the rats were no longer able to take the preparation orally. In the control group, the same operations were conducted, except for the application of the preparation.

Test results are shown in FIG. 1. The preparation of Example 4 significantly inhibited the edema induced by subcutaneous administration of carrageenin from 2 to 4 hours after administration of the carregeenin. The swelling rate was lower than that of Comparative Examples 4 and 5 up to 4 hours from the administration of the carrageenin. The swelling rate of Example 4 at 4 hours from the induction was 14.8% (the inhibition rate to the control group was 70.2%) which was the lowest while the swelling rate (and the inhibiting rate in the same sense as above) of Comparative Examples 4 and 5 were 25.4% (47.7%) and 35.6% (26.7%), respectively.

2-2 Test on Pain Reaction of Inflammatory Paw Induced by Yeast
(Randall and Selitto Method)

Analgesic action of the anti-inflammatory and analgesic preparation for external use according to this invention (Example 4) and of commercial products of another company (Comparative Examples 4 and 5) were evaluated by a test on pain reaction of inflammatory paw induced by yeast. Thus, 0.1 ml of a 20% yeast suspension was subcutaneously administered to the right hind paws of Wistar strain rats (male; 5 weeks of age) so that inflammation was induced. After 2 hours, the pain threshold value of the inflammatory paw was measured using a threshold value measuring device of a compression type (MK-800; manufactured by Muromachi Kikai K.K.). Animals having a pain threshold of the yeast-induced inflammatory paw of not more than 50% of the value before the injection were selected and were divided into five groups (each group consisting of eight rats) so as to make the mean value of the pain threshold value in each group approximately equal. Each preparation (50 mg) was applied around the site where the yeast was administered and the pain threshold value of the inflammatory paw after 1, 2, 4 and 8 hours from the administration was measured. Incidentally, after application of the preparation, the site of administration was covered with a wrapping film and an expandable adhesive tape was applied thereon to fix it in place, so that the rats were no longer able to take the preparation orally. In control groups, the same operations were conducted except for the application of the preparation. The test results are shown in FIG. 2.

As compared to the control group, the composition of Example 4 significantly raised the pain threshold value, which had been lowered by subcutaneous administration of yeast, during the 1 to 6 hour period following its application. The pain threshold value after one hour from the application showed the highest value (69.4 g) and maintained the values of about 1.7–2.2-fold of those of the control until 6 hours. Comparative Examples 4 and 5 similarly raised the threshold values significantly until 6 hours, but the pain threshold values after one hour from the application were 51.9 and 65.6 g for Comparative Examples 4 and 5, respectively, which were lower than the results obtained with the composition of Example 4.

From the above results of the pharmacological tests, application of the product according to this invention to the inflammatory site showed quicker onset of the effect as compared with other anti-inflammatory and analgesic preparations. Moreover, the pharmaceutical effect was very good and was maintained for 4 to 6 hours after application.

Test Example 3

Evaluation of Safety by Application to Human Being

Safety of the anti-inflammatory and analgesic composition for external use according to this invention (Example 4) and the competitive products of another company (Comparative Examples 4 and 5) in human healthy skin was investigated by an open patch test and a closed patch test by a closed sticking for 24 hours. The test was conducted by 18 healthy male adults (age: 20–24, 21.8 in average) and 18 females (age: 20–45; 25.8 in average). In an open patch test, a circle with 1 cm diamater was drawn on the inner side of the upper arm of the persons to be tested, a preparation was uniformly applied within the circle using an applicator in accordance with a previously-fixed allotting table of the compositions and then determinations were made after 20 minutes, 24 hours and 48 hours. In a closed patch test, a sample was permeated into a filter paper placed on a fin chamber and subjected to a closed adhesion to the inner side of the upper arm using a Scanpor tap for 24 hours in accordance with a previously-fixed allotting table. Judgement was made after 60 minutes and also 24 hours from the removal of the sample. Both judgements were conducted in accordance with the standard regulated by the Patch Test Study Association of Japan as mentioned below.

| Criteria for judgement according to the Patch Test Study Association of Japan | |
|---|---|
| No reaction | ; (−) |
| Slight red spots | ; (1) |
| Apparent red spots | ; (+) |
| Red spots + Swelling | ; (++) |
| Red spots + Swelling + Papules or Vesicles | ; (+++) |
| Big vesicles | ; (++++) |

In the case where apparent allergy reaction was noted, the corresponding score was marked with a circle.

Results of the adhesion test are shown in Table 2 (open patch test) and in Table 3 (closed patch test). In the open patch test, no reaction was noted on the skin [in] with any of the preparations tested. In the closed patch test, one case of apparent red spots (+) was noted with Comparative Example 5 after 60 minutes from the removal. After 24 hours from the removal one case of apparent red spots (+) was noted for each of Examples 4 and 5. While in Example 4, only slight red spots (±) were noted. Table 3 shows stimulation indexes calculated from the results of the closed patch test. From this result, it is apparent that the compositions of Examples 4 and 5 are included within a category of allowable products. From the above, it can be concluded that the compositions of Examples 4 and 5 would encounter no problem in actual use, because, in the open patch test, which is close to the situation of actual use, no positive reaction was noted at all while, in the closed patch test, using a fin chamber, stimulation is apt to occur, as compared with actual use, but the degree of the stimulation is similar to or less than that of the commercially available preparations.

TABLE 2

Open patch test

| | Judging Time | | | | | | | | |
|---|---|---|---|---|---|---|---|---|---|
| | Judgement 20 minutes after application | | | Judgement 24 hours after application | | | Judgement 48 hours after application | | |
| | Positive rating | | | | | | | | |
| Sample | ≧++ | ≧+ | ≧± | ≧++ | ≧+ | ≧± | ≧++ | ≧+ | ≧± |
| Example 4 | 0/36 | 0/36 | 0/36 | 0/36 | 0/36 | 0/36 | 0/36 | 0/36 | 0/36 |
|  | 0% | 0% | 0% | 0% | 0% | 0% | 0% | 0% | 0% |
| Example 5 | 0/36 | 0/36 | 0/36 | 0/36 | 0/36 | 0/36 | 0/36 | 0/36 | 0/36 |
|  | 0% | 0% | 0% | 0% | 0% | 0% | 0% | 0% | 0% |
| Comparative Example 4 | 0/36 | 0/36 | 0/36 | 0/36 | 0/36 | 0/36 | 0/36 | 0/36 | 0/36 |
|  | 0% | 0% | 0% | 0% | 0% | 0% | 0% | 0% | 0% |
| Comparative Example 5 | 0/36 | 0/36 | 0/36 | 0/36 | 0/36 | 0/36 | 0/36 | 0/36 | 0/36 |
|  | 0% | 0% | 0% | 0% | 0% | 0% | 0% | 0% | 0% |

TABLE 3

Closed patch test

| | Judging Time | | | | | |
|---|---|---|---|---|---|---|
| | Judgement 60 minutes after removal | | | Judgement 24 hours after removal | | |
| | Positive rating | | | | | |
| Sample | ≧++ | ≧+ | ≧± | ≧++ | ≧+ | ≧± |
| Example 4 | 0/36 | 0/36 | 3/36 | 0/36 | 0/36 | 3/36 |
|  | 0% | 0% | 8.3% | 0% | 0% | 8.3% |
| Example 5 | 0/36 | 0/36 | 5/36 | 0/36 | 1/36 | 5/36 |
|  | 0% | 0% | 13.9% | 0% | 2.8% | 13.9% |
| Comparative Example 4 | 0/36 | 0/36 | 4/36 | 0/36 | 1/36 | 1/36 |
|  | 0% | 0% | 11.1% | 0% | 2.8% | 2.8% |
| Comparative Example 5 | 0/36 | 1/36 | 11/36 | 0/36 | 1/36 | 12/36 |
|  | 0% | 2.8% | 30.6% | 0% | 2.8% | 33.3% |

TABLE 4

Stimulation Indexes

| | Judging time | |
|---|---|---|
| Sample | 60 minutes after removal | 24 hours after removal |
| Example 4 | 4.2 | 4.2 |
| Example 5 | 6.9 | 9.7 |
| Comparative Example 4 | 5.6 | 4.2 |
| Comparative Example 5 | 18.1 | 19.4 |

What is claimed:

1. An anti-inflammatory analgesic pharmaceutical topical composition comprising
   (a) an anti-inflammatory and analgesic effective amount of a non-steroidal anti-inflammatory and analgesic agent;
   (b) a skin penetration enhancer selected from the group consisting of oleic acid, oleyl alcohol and mixtures thereof, the enhancer being present in an amount sufficient to enhance skin penetration of the non-steroidal anti-inflammatory and analgesic agent, as compared to a like composition that does not contain the enhancer; and
   (c) a pharmaceutically acceptable vehicle for the non-steroidal anti-inflammatory and analgesic agent and the skin penetration enhancer consisting of 15 to 70 weight %, based on the total weight of the composition, of a monohydric saturated aliphatic alcohol containing 1 to 4 carbon atoms; 0.1 to 30 weight %, based on the total weight of the composition, of a polyhydric alcohol selected from the group consisting of saturated aliphatic glycols containing 2 to 4 carbon atoms and glycerol; and 10 to 60 weight %, based on the total weight of the composition, of water.

2. The composition, as claimed in claim 1, further including 0.5 to 5 weight %, based on the total weight of the composition, of menthol.

3. The composition, as claimed in claim 2, wherein the menthol is 1-menthol.

4. The composition, as claimed in claim 1, wherein the non-steroidal anti-inflammatory and analgesic agent is present in an amount of 0.1 to 10 weight %, based on the total weight of the composition.

5. The composition, as claimed in claim 1, wherein the non-steroidal anti-inflammatory and analgesic agent is present in an amount of 0.5 to 5 weight %, based on the total weight of the composition.

6. The composition, as claimed in claim 1, wherein the enhancer is present in an amount of 0.1 to 15 weight %, based on the total weight of the composition.

7. The composition, as claimed in claim 1, wherein the enhancer is present in an amount of 0.5 to 10 weight %, based on the total weight of the composition.

8. The composition, as claimed in claim 1, further including 0.1 to 5 weight %, based on the total weight of the composition, of a gelling agent.

9. The composition, as claimed in claim 8, wherein the gelling agent is carboxyvinyl polymer, sodium carboxymethyl cellulose, polyvinyl alcohol, methyl cellulose, hydroxyethyl cellulose, hydroxypropyl cellulose, polyvinyl pyrrolidone or hydroxypropyl methylcellulose.

10. The composition, as claimed in claim 1, wherein the monohydric saturated aliphatic alcohol is ethanol or isopropanol.

11. The composition, as claimed in claim 1, wherein the polyhydric alcohol is glycerol.

12. The composition, as claimed in claim 1, wherein the enhancer is cis-oleic acid.

13. The composition, as claimed in claim 1, wherein the non-steroidal anti-inflammatory and analgesic agent is ketoprofen, indomethacin, bufexamac, ibuprofen or piroxicam.

* * * * *